United States Patent [19]

Emorine et al.

[11] Patent Number: 5,288,607
[45] Date of Patent: Feb. 22, 1994

[54] POLYPEPTIDES HAVING A β-ADRENERGIC RECEPTOR ACTIVITY IN MAN, IMPLICATED IN THE LIPOLYTIC RESPONSE, NUCLEIC ACIDS CODING FOR THESE POLYPEPTIDES AND THE USE OF THESE POLYPEPTIDES FOR THE SCREENING OF A SUBSTANCE ACTIVE ON THESE POLYPEPTIDES

[75] Inventors: Laurent Emorine; Stefano Marullo; Donny Strosberg, All of Paris, France

[73] Assignee: Centre National De La Recherche Scientifique, Paris, France

[21] Appl. No.: 721,571

[22] PCT Filed: Jan. 25, 1990

[86] PCT No.: PCT/FR90/00054
§ 371 Date: Sep. 3, 1991
§ 102(e) Date: Sep. 3, 1991

[87] PCT Pub. No.: WO90/08775
PCT Pub. Date: Aug. 9, 1990

[30] Foreign Application Priority Data

Jan. 25, 1989 [FR] France ............................... 8900918

[51] Int. Cl.[5] .................... C12Q 1/68; C12P 21/06; C07K 3/00; C07H 15/12
[52] U.S. Cl. ......................................... 435/6; 435/7.1; 435/7.21; 435/7.37; 435/69.1; 435/240.2; 435/252.3; 435/320.1; 530/350; 530/359; 530/387.1; 530/397; 530/403; 536/23.1; 536/23.5; 536/24.31

[58] Field of Search .................. 435/69.1, 6, 7.1, 7.21, 435/7.37, 240.2, 252.3, 320.1; 530/350, 387.1, 397, 403, 359; 536/27, 22.1, 23.1, 23.5, 24.31

[56] References Cited

PUBLICATIONS

Bahouth et al. "Subclassification of β-Adreng. Recept. . . ." Molecular Pharmacology 34:318-326 1988.
Arch et al. "Atypical β-adrenoreceptor on brown . . ." Nature vol. 309 pp. 163-165 (1984).
Emorine et al. "Structure of the gene for human $\beta_2$-adrenergic . . ." PNAS vol. 84 pp. 6995-6999 (1987).
Yarden et al. "Avian β-adrenergic receptor: Primary Structure. . . " PNAS vol. 83, pp. 6795-6799 (1986).
Lerner; Richard "Tapping the immunological repertoire . . ." Nature vol. 299 pp. 592-596 (Oct. 14, 1982).

*Primary Examiner*—Robert A. Wax
*Assistant Examiner*—Hyosuk Kim
*Attorney, Agent, or Firm*—Keck, Mahin & Cate

[57] ABSTRACT

Novel polypeptides having a β-adrenergic receptor activity containing the sequence of 402 amino acids, or a fragment of this sequence, said fragment being such that, in particular, either it nonetheless includes the sites contained in said sequence and whose presence is necessary so that, when the fragment is exposed to the surface of a cell, it is capable of participating in the activation of the cyclase adenylate in the presence of an agonist, or it is likely to be recognized by antibodies which also recognize the above succession of 402 amino acids, but fail to recognize the β1 adrenergic receptor and the β2 adrenergic receptor. These polypeptides are useful for screening drugs which act on said polypeptides and for treating obesity, fat diabetes and hyperlipidemias.

16 Claims, 9 Drawing Sheets

FIG.1A

```
agatctcaccaagctgaggtcttgggagaggagatactggctgagccctattacttaatt    60 taaaataccttaggggaggccacccaagtggatgcggggctggtgtgaatcctttgcttg   120 actccagcgggttacctttgcctctgatacataaagggtggggatgggagcgctctcctc   180 tctccttcccctgccttgctgtgggaacttctgggaaaggaggtgcagggctccaggaag   240 ccagtgcccagggagtgctatgctgagtccaggagcctggccacggcaggggtggacaga   300 tggtggcagaggaaccacggtgtcccttcctccagatttagctaaaggaaacgtggagca   360 tcccattggccatcctccccactctccaattcggctccagaggcccctccagactatagg   420 cagctgccccttttaagcgtcgctactcctcccccaagagcggtggcaccgagggagttgg   480 ggtgggggggaggctgagcgctctggctgggacagctagagaagatggcccaggctgggga   540 agtcgctctcatgccttgctgtcccctccctgagccaggtgatttgggagacccctcc    600
```

|  |  |  |  |  | Met | Ala | Pro | Trp | Pro |   5 |
|---|---|---|---|---|---|---|---|---|---|---|
| ttccttctttccctaccgccccacgcgcgacccgggg | | | | | ATG | GCT | CCG | TGG | CCT | 652 |
| His | Glu | Asn | Ser | Ser | Leu | Ala | Pro | Trp | Pro | Asp | Leu | Pro | Thr | Leu |  20 |
| CAC | GAG | AAC | AGC | TCT | CTT | GCC | CCA | TGG | CCG | GAC | CTC | CCC | ACC | CTG | 697 |
| Ala | Pro | Asn | Thr | Ala | Asn | Thr | Ser | Gly | Leu | Pro | Gly | Val | Pro | Trp |  35 |
| GCG | CCC | AAT | ACC | GCC | AAC | ACC | AGT | GGG | CTG | CCA | GGG | GTT | CCG | TGG | 742 |
| Glu | Ala | Ala | Leu | Ala | Gly | Ala | Leu | Leu | Ala | Leu | Ala | Val | Leu | Ala |  50 |
| GAG | GCG | GCC | CTA | GCC | GGG | GCC | CTG | CTG | GCG | CTG | GCG | GTG | CTG | GCC | 787 |
| Thr | Val | Gly | Gly | Asn | Leu | Leu | Val | Ile | Val | Ala | Ile | Ala | Trp | Thr |  65 |
| ACC | GTG | GGA | GGC | AAC | CTG | CTG | GTC | ATC | GTG | GCC | ATC | GCC | TGG | ACT | 832 |

FIG.1B-1

```
Pro Arg Leu Gln Thr Met Thr Asn Val Phe Val Thr Ser Leu Ala    80
CCG AGA CTC CAG ACC ATG ACC AAC GTG TTC GTG ACT TCG CTG GCC   877

Ala Ala Asp Leu Val Met Gly Leu Leu Val Val Pro Pro Ala Ala    95
GCA GCC GAC CTG GTG ATG GGA CTC CTG GTG GTG CCG CCG GCG GCC   922

Thr Leu Ala Leu Thr Gly His Trp Pro Leu Gly Ala Thr Gly Cys   110
ACC TTG GCG CTG ACT GGC CAC TGG CCG TTG GGC GCC ACT GGC TGC   967

Glu Leu Trp Thr Ser Val Asp Val Leu Cys Val Thr Ala Ser Ile   125
GAG CTG TGG ACC TCG GTG GAC GTG CTG TGT GTG ACC GCC AGC ATC  1012

Glu Thr Leu Cys Ala Leu Ala Val Asp Arg Tyr Leu Ala Val Thr   140
GAA ACC CTG TGC GCC CTG GCC GTG GAC CGC TAC CTG GCT GTG ACC  1057

Asn Pro Leu Arg Tyr Gly Ala Leu Val Thr Lys Arg Cys Ala Arg   155
AAC CCG CTG CGT TAC GGC GCA CTG GTC ACC AAG CGC TGC GCC CGG  1102

Thr Ala Val Val Leu Val Trp Val Val Ser Ala Ala Val Ser Phe   170
ACA GCT GTG GTC CTG GTG TGG GTC GTG TCG GCC GCG GTG TCG TTT  1147

Ala Pro Ile Met Ser Gln Trp Trp Arg Val Gly Ala Asp Ala Glu   185
GCG CCC ATC ATG AGC CAG TGG TGG CGC GTA GGG GCC GAC GCC GAG  1192

Ala Gln Arg Cys His Ser Asn Pro Arg Cys Cys Ala Phe Ala Ser   200
GCG CAG CGC TGC CAC TCC AAC CCG CGC TGC TGT GCC TTC GCC TCC  1237

Asn Met Pro Tyr Val Leu Leu Ser Ser Ser Val Ser Phe Tyr Leu   215
AAC ATG CCC TAC GTG CTG CTG TCC TCC TCC GTC TCC TTC TAC CTT  1282

Pro Leu Leu Val Met Leu Phe Val Tyr Ala Arg Val Phe Val Val   230
CCT CTT CTC GTG ATG CTC TTC GTC TAC GCG CGG GTT TTC GTG GTG  1327

Ala Thr Arg Gln Leu Arg Leu Leu Arg Gly Glu Leu Gly Arg Phe   245
GCT ACG CGC CAG CTG CGC TTG CTG CGC GGG GAG CTG GGC CGC TTT  1372
```

FIG. 1B-2

```
Pro Pro Glu Glu Ser Pro Pro Ala Pro Ser Arg Ser Leu Ala Pro    260
CCG CCC GAG GAG TCT CCG CCG GCG CCG TCG CGC TCT CTG GCC CCG   1417

Ala Pro Val Gly Thr Cys Ala Pro Pro Glu Gly Val Pro Ala Cys    275
GCC CCG GTG GGG ACG TGC GCT CCG CCC GAA GGG GTG CCC GCC TGC   1462

Gly Arg Arg Pro Ala Arg Leu Leu Pro Leu Arg Glu His Arg Ala    290
GGC CGG CGG CCC GCG CGC CTC CTG CCT CTC CGG GAA CAC CGG GCC   1507

Leu Cys Thr Leu Gly Leu Ile Met Gly Thr Phe Thr Leu Cys Trp    305
CTG TGC ACC TTG GGT CTC ATC ATG GGC ACC TTC ACT CTC TGC TGG   1552

Leu Pro Phe Phe Leu Ala Asn Val Leu Arg Ala Leu Gly Gly Pro    320
TTG CCC TTC TTT CTG GCC AAC GTG CTG CGC GCC CTG GGG GGC CCC   1597

Ser Leu Val Pro Gly Pro Ala Phe Leu Ala Leu Asn Trp Leu Gly    335
TCT CTA GTC CCG GGC CCG GCT TTC CTT GCC CTG AAC TGG CTA GGT   1642

Tyr Ala Asn Ser Ala Phe Asn Pro Leu Ile Tyr Cys Arg Ser Pro    350
TAT GCC AAT TCT GCC TTC AAC CCG CTC ATC TAC TGC CGC AGC CCG   1687

Asp Phe Arg Ser Ala Phe Arg Arg Leu Leu Cys Arg Cys Gly Arg    365
GAC TTT CGC AGC GCC TTC CGC CGT CTT CTG TGC CGC TGC GGC CGT   1732

Arg Leu Pro Pro Glu Pro Cys Ala Ala Ala Arg Pro Ala Leu Phe    380
CGC CTG CCT CCG GAG CCC TGC GCC GCC GCC CGC CCG GCC CTC TTC   1777

Pro Ser Gly Val Pro Ala Ala Arg Ser Ser Pro Ala Gln Pro Arg    395
CCC TCG GGC GTT CCT GCG GCC CGG AGC AGC CCA GCG CAG CCC AGG   1822

Leu Cys Gln Arg Leu Asp Gly                                    402
CTT TGC CAA CGG CTC GAC GGG TAGgtaaccggggcagagggaccggcggctca  1875 gggtcgggaagcatgcgatgtgtccgtgggtcaactttttgagtgtggagtttattaaga  1935 gaaggtgggatggctttgcttggagagaaaagggaacgaggagtagcgaaccaaaatggg  1995 acccagggtccttttctttccggatcc                                   2022
```

POLYPEPTIDES HAVING A β-ADRENERGIC RECEPTOR ACTIVITY IN MAN, IMPLICATED IN THE LIPOLYTIC RESPONSE, NUCLEIC ACIDS CODING FOR THESE POLYPEPTIDES AND THE USE OF THESE POLYPEPTIDES FOR THE SCREENING OF A SUBSTANCE ACTIVE ON THESE POLYPEPTIDES

FIELD OF THE INVENTION

The present invention relates to polypeptides having a β-adrenergic receptor activity in man, and more particularly implicated in the lipolytic response of the adipose tissues, and the genes coding for these polypeptides.

The invention also relates:

to vectors containing the genes coding for polypeptides having a β-adrenergic activity, to cell hosts transformed by genes coding for the above-mentioned polypeptides, to nucleotide probes capable of hybridizing with the genes coding for the above-mentioned polypeptides, to polyclonal and monoclonal antibodies directed against the above-mentioned polypeptides and which can be used for the purpose of in vitro diagnosis, to kits for studying the degree of affinity of certain substances for the above-mentioned polypeptides, to medicines containing substances active on the above-mentioned polypeptides having a β-adrenergic receptor activity, and more particularly designed for the treatment of obesity, diabetes and hyperlipidemia.

BACKGROUND OF THE INVENTION

The catecholamines such as adrenalin and noradrenalin, the synthetic agonists of these catecholamines which mimic their biological function and the antagonists which block these functions exert their effects by binding to specific recognition sites (adrenergic receptors) situated on cell membranes.

Two main classes of adrenergic receptors have been defined, the α adrenergic receptors and the β adrenergic receptors.

Within the set of these two classes, four sub-types of these receptors for catecholamines are distinguished (α1, α2, β1 and β2-AR). Their genes have recently been isolated and identified (5-8). The analysis of these genes has made it possible to recognize that they belong to a family of integral membrane receptors exhibiting certain homologies (9-10), in particular at the level of the 7 transmembrane regions. These latter are coupled to regulatory proteins, called G proteins, capable of binding molecules of guanosine triphosphate (GTP).

More precisely, the G proteins are proteins having the capacity to intervene structurally and functionally between receptors and enzymes catalysing the production of intracellular mediators (such as adenylate cyclase, guanylate cyclase, the phospholipases, the kinases) or between receptors and ion channels, the controlled opening of which brings about a flux of ions (such as calcium, potassium, sodium, hydrogen ions) into the cell.

These proteins have transduction and coupling functions.

The above-mentioned family of receptors is designated as the "R$_7$G family" (10). It comprises, in particular, acetylcholine muscarinic receptors, serotonin receptors, receptors for neuropeptides, substance K and angiotensin II and the visual receptors for the family of the opsins (9-10).

Up until very recently, the definition of the sub-types of receptors was based mainly on the analysis of the physiological properties and binding of different ligands in heterogenous systems. In the R$_7$G family, several genes coding for sub-types of receptors defined by their pharmacological properties have been cloned and characterized. Probes obtained from these genes have made it possible to identify additional receptor sub-types (11-12).

The precise nature of the β-adrenergic receptor, which is capable of modulating physiological functions such as thermogenesis in adipose cells as well as intestinal relaxation has remained obscure. In connection with this latter property, it has been found that isoproterenol still inhibits the contractions of the guinea pig ileum induced by the cholinergic pathway (3), in spite of the total blockage of the known adrenergic receptors of the α and β types with pentholamine and propanolol.

By undertaking a detailed study of the physiological effects of the agonists and of the inhibition by the antagonists of the polypeptides having a β-adrenergic receptor activity (1-3), the hypothesis has been put forward of the existence of a novel sub-type of β-adrenergic receptor.

This hypothesis has been challenged by a conflicting hypothesis, resulting from the analysis of the β-receptor content of an adipose tissue by means of binding studies. This analysis has led to the conclusion—which constitutes the most recent state of the art—that the lipolytic β-adrenergic receptors are uniquely of the β1 sub-type (13).

Moreover, among the compounds used in the modern pharmacopeia, a dominant position is occupied by the β-adrenergic agonists or antagonists (β1 or β2-AR). In spite of their remarkable efficacy, the available medicines can produce side effects, due potentially to the interaction with other homologous receptors.

SUMMARY OF THE INVENTION

The invention raises an uncertainty with regard to the hypothesis, previously formulated but subsequently ruled out, of the existence of polypeptides having a β-adrenergic receptor activity other than that of the β1 and β2 receptors. In fact, it provides access to novel polypeptides having a β-adrenergic receptor activity which does not have similarities to that of the β1-adrenergic receptors or that of the β2-adrenergic receptors.

The object of the invention is also screening procedures for new medicines acting on the novel polypeptides having a β-adrenergic receptor action and designed, among other things, for the treatment of obesity, fatty diabetes and diabetes in non insulin-dependent subjects, as well as for the treatment of hyperlipidemias.

In particular, the novel polypeptide of the invention having a β-adrenergic activity:

contains the sequence of 402 amino acids of FIG. 12 or a fragment of this sequence, this fragment being such that either it contains nonetheless the sites contained in this sequence, whose presence is necessary so that, when this fragment is exposed to the surface of a cell, it is capable of participating in the activation of the adenylate cyclase in the presence of an agonist, this activation increasing in the order of the following agonists: salbutamol, BRL 28410, BRL 37344 and (1)-isoproterenol, or it is capable of being recognized by antibodies which also recognize the above-mentioned sequence of 402 amino acids, but which do not recognize either the β1 adrenergic receptor or the β2 adrenergic receptor or it is capable of generating antibodies which recognize the above-mentioned sequence of 402 amino acids but which do not recognize the β1 receptor or the β2 adrenergic receptor.

The recognition of the above-mentioned sequence of 402 amino acids by the above-mentioned antibodies—or of the above-mentioned fragment by the above-mentioned antibodies—means that the above-mentioned sequence forms a complex with one of the above-mentioned antibodies.

The formation of the antigen (i.e. sequence of 402 amino acids or the above-mentioned fragment)—antibody complex and the detection of the existence of a complex formed can be done in the following manner: the antigen and antibody are allowed to incubate for 1 h at room temperature, then overnight at 4° C. in PLT buffer;

the PLT buffer has the following composition: 10 mM of sodium phosphate, 145 mM of NaCl, 5% of lyophilized skimmed milk (wt/v), 0.1% of Tween 20 (v/v), the pH being 7.4, four 5 min. washings with the PLT buffer are then carried out, a second biotinylated antibody is allowed to incubate for 1 h at room temperature in PLT buffer, four 5 min. washings with PLT buffer are carried out, streptavidin peroxidase is allowed to incubate for 1 h at room temperature in PLT buffer, four washing with PLT buffer are undertaken, then a washing is carried out with the medium constituted by: 10 mM sodium phosphate, 145 mM of NaCl, 0.1% of Triton X 100, the pH being 7.4, a further washing is carried out with the medium having the composition indicated above but not containing Triton X 100, then the antigen-antibody complex formed is revealed by standard procedures.

As for the definition of the "fragments containing the sites" and complying with the above-mentioned definition, reference should be made to the description given hereinafter.

The novel β-adrenergic receptors of the invention are thus characterized by properties different from those of the β1 and β2 receptors in that they behave differently towards substances respectively antagonists and agonists of β1 and β2.

Figure 2A:
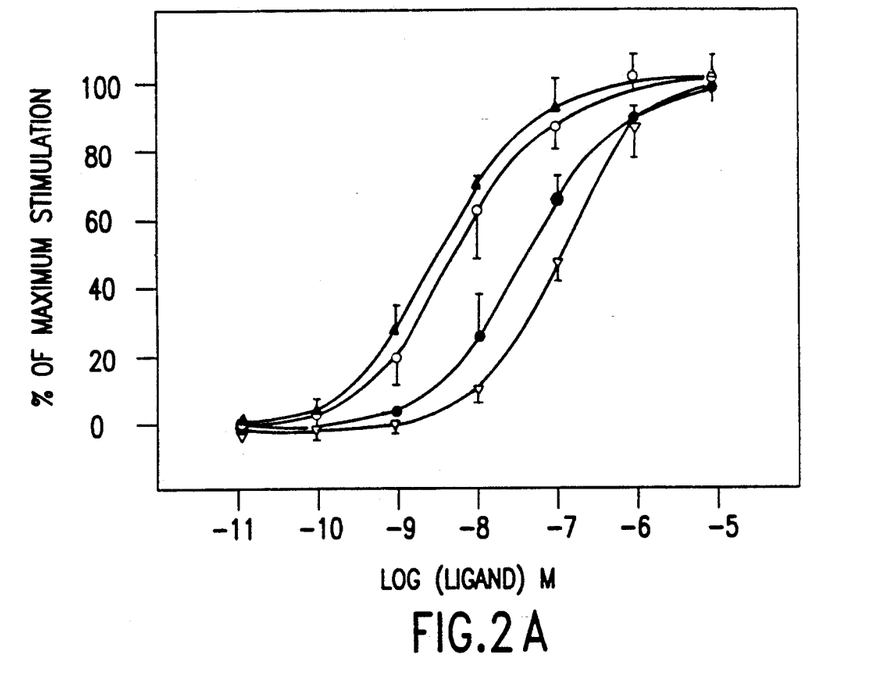
FIGS. 2A, 2B, 2C, 2D and 2E represent, graphically, the accumulation of cyclic AMP in CHO-β3 cells after exposure to various agents.
Figure 2B:
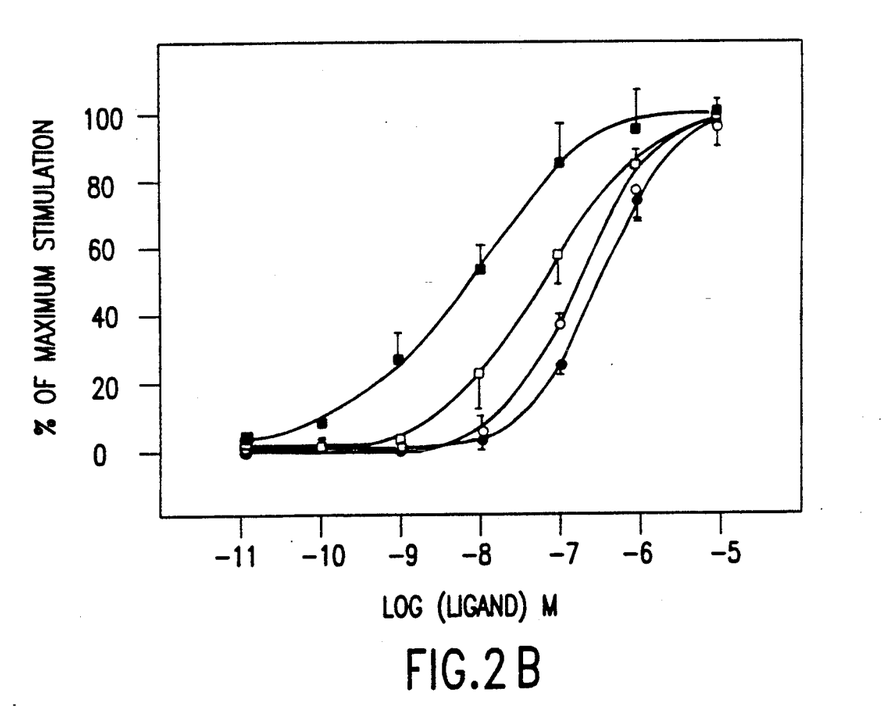
Figure 2C:
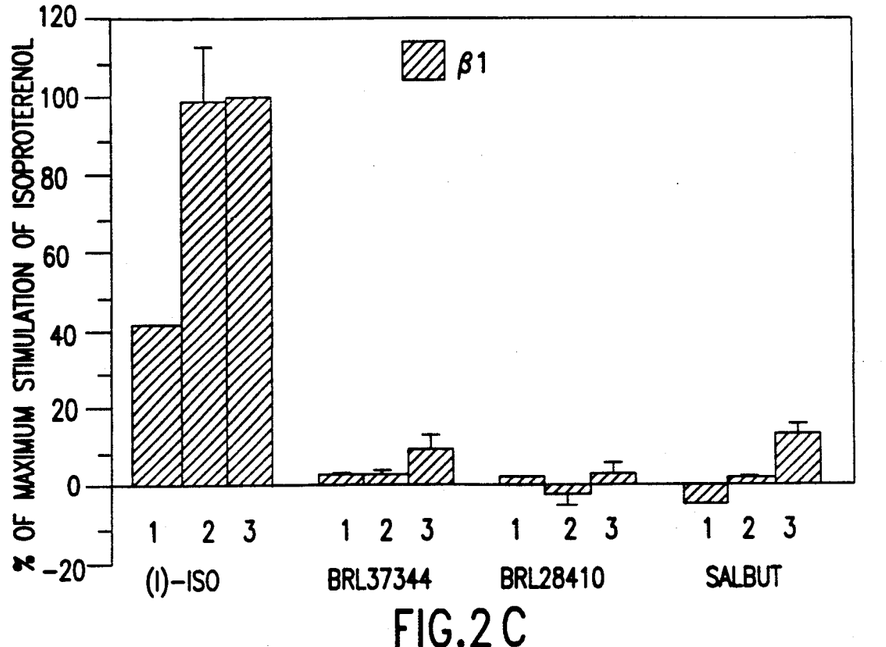

The determination of the order in which the polypeptides of the invention participate in the activation of the adenylate cyclase in the presence of the agonists present: salbutamol, BRL 28410, BRL 37344 and (1)-isoproterenol, is described in the comment relating to FIG. 2C, which follows the present description.

The order indicated above is totally different from that obtained with the same agonists when the responses are mediated by the intermediary of the β1 or β2 adrenergic receptors.

In the case of "β3-CHO" cells defined below, this order is similar to that determined for the stimulation of lipolysis in rat adipose cells (1). The only difference is constituted by the relative order of isoproterenol and BRL 37344. However, the isoproterenol referred to in the invention is the levo-rotatory isomer of isoproterenol whereas that of reference (1) is the racemic mixture (d1).

BRL 28410 is defined in reference (1) and has the following structure:

BRL 37344 is defined in reference (1) and has the following structure:

The invention also relates to chimeric proteins in which the polypeptide as defined above or parts of the latter are joined to a chain of amino acids which is heterologous with respect to this polypeptide.

Advantageous chimeric proteins of the invention are constituted by those in which the heterologous chain of amino acids is selected from the sequence of the β1 adrenergic receptor or a fragment of this receptor or the sequence of the β2-adrenergic receptor or a fragment of this receptor.

The chimeric polypeptides and proteins of the invention may be glycosylated and may or may not contain disulfide bridges.

For the purposes of simplification, the polypeptides of the invention will be designated by "β3 receptors" in the remainder of the description.

The β3 receptors of the invention are also such that the capacity to stimulate the adenylate cyclase and/or the accumulation of cyclic AMP induced by isoproterenol and are not inhibited by the following compounds:
practolol,
nadolol,
CGP 12,177 butoxamine,
alprenolol,
propanolol,
pindolol,
oxprenolol,
used at concentrations lower than or equal to $10^{-4}$M under the following conditions:

as far as the accumulation of cyclic AMP is concerned, cells are cultivated and harvested after treatment with Versene/EDTA (Eurobio, Paris), washed and resuspended in a Hank medium containing 20 mM of Hepes buffered at pH 7.4, 1 mM ascorbic acid and 0.1 mM isobutyl-methyl-zanthine; aliquots of $10^6$ cells are incubated for 30 minutes with the inhibitors at $10^{-4}M$ before the addition of $5.10^{-9}M$ of isoproterenol; the incubation is continued for a further 30 minutes and the cyclic AMP levels are measured according, for example, to the specifications of the Amersham assay kit.

The stimulation of the adenylate cyclase by the $\beta 3$ receptors of the invention as well as the measurement of the accumulation of cAMP may be carried out according to standard methods.

The CGP12,177 is a compound manufactured by the CIBA-GEIGY company.

The conditions used are similar to those under which the above-mentioned compounds behave as antagonists towards $\beta 1$ and $\beta 2$ adrenergic receptors.

The $\beta 3$ receptors of the invention are also such that pindolol and oxprenolol stimulate the accumulation of cyclic AMP in CHO cells transfected with the above-mentioned $\beta 3$ receptor under the following conditions:

as far as the accumulation of cyclic AMP is concerned, cells are cultivated and harvested after treatment with Versene/EDTA (Eurobio, Paris), washed and resuspended in a Hank medium containing 20 mM of Hepes buffered at pH 7.4, 1 mM ascorbic acid and 0.1 mM isobutyl-methyl-xanthine; aliquots of $10^6$ cells are incubated for 30 minutes in a total volume of 1 ml with concentrations of pindolol or oxprenolol higher than $10^{-11}M$ and the cAMP levels are measured according, for example, to the specifications of the Amersham assay kit.

Figure 1B:
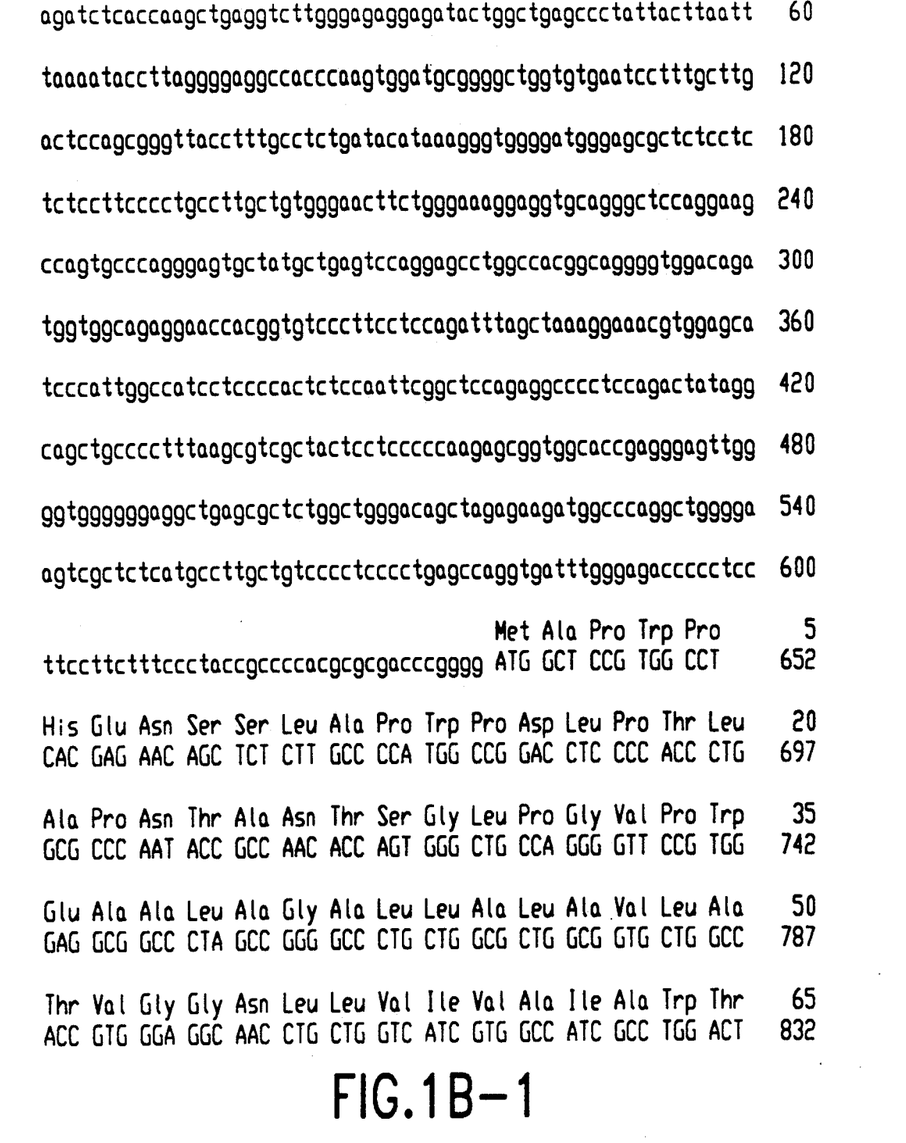

An advantageous $\beta 3$ receptor of the invention is constituted by the chain of amino acids 1 to 402 shown in FIG. 1a.

This $\beta 3$ receptor is considered to contain seven hydrophobic transmembrane regions separated by intra- and extra-cellular hydrophilic loops.

The invention also relates to the variant polypeptides which correspond to the polypeptides defined above bearing certain localized mutations without the polypeptides losing the properties of the $\beta 3$-adrenergic receptor. Among these peptides, mention may be made of those which are recognized by antibodies recognizing the transmembrane regions as well as those which are recognized by antibodies recognizing the regions other than the transmembrane regions.

The invention also relates to nucleic acids which comprise or which are constituted by a chain of nucleotides coding for any one of the previously defined $\beta 3$ receptors.

More particularly, the invention relates to the nucleic acid which comprises the chain of nucleotides shown in FIG. 1b, extending from the end constituted by the nucleotide at position 1 to that constituted by the nucleotide at position 2022.

The invention also relates to the nucleic acid shown in FIG. 1b comprising or being constituted by the chain extending from the end constituted by the nucleotide at position 638 to that constituted by the nucleotide at position 1843.

The nucleic acid defined above corresponds to the part coding for the gene corresponding to that polypeptide shown in FIG. 1a.

Also included in the invention are the nucleic acids which vary with respect to those defined above and which bear certain localized mutations to the extent that these variant nucleic acids hybridize with the nucleic acids previously defined or with the nucleic acid probes defined hereafter under the conditions of hybridization defined hereafter in the description.

The nucleic acids of the invention may be prepared either by a chemical process or by other processes.

A suitable method of preparation of the nucleic acids (containing a maximum of 200 nucleotides—or bp, when double-stranded nucleic acids are concerned) of the invention by the chemical route comprises the following steps:

the synthesis of DNA using the automated $\beta$-cyanoethyl phosphoramidite method described in *Bioorganic Chemistry* 4; 274-325, 1986, the cloning of the DNAs thus obtained in a suitable plasmid vector and the recovery of the DNAs by hybridization with a suitable probe.

A chemical method of preparation of nucleic acids longer than 200 nucleotides—or bp (when double-stranded nucleic acids are concerned) comprises the following steps:

the assembly of chemically synthesized oligonucleotides provided at their ends with various restriction sites, the sequences of which are compatible with the chain of amino acids of the natural polypeptide according to the principle described in *Proc. Natl. Acad. Sci. USA* 80; 7461-7465, 1983, the cloning of the DNAs thus obtained into a suitable plasmid vector and the recovery of the desired nucleic acid by hybridization with a suitable probe.

Another process for the preparation of the nucleic acids of the invention from mRNA comprises the following steps:

preparation of cellular RNA from any tissue expressing the $\beta 3$-adrenergic receptor, in particular adipose, muscular, hepatic and intestinal tissues, according to the procedures described by Maniatis et al. in "Molecular cloning", Cold Spring Harbor Laboratory, 1982, and Ausubel F. M., Brent T., Kingston R. E., Moore D. D., Smith J. A., Seidman J. G. and Struhl K. (1989) *Current Protocols in Molecular Biology*, chapter 4, Greene Publishing Associates and Wiley-Interscience, New York, recovery and purification of the mRNAs by passage of the total cellular RNAs through chromatography column containing immobilized oligo dT, synthesis of a cDNA strand starting from the purified mRNAs according to the procedure described in Gene 25:263, 1983, cloning of the nucleic thus obtained in a suitable plasmid vector and recovery of the desired nucleotide sequence using a suitable hybridization probe.

In order to prepare the nucleic acids of the invention, the chemically synthesized oligonucleotide hybridization probes are the following:

that defined by the nucleic acid sequence shown in FIG. 1b, extending from the end constituted by the nucleotide at position 1 to that constituted by the nucleotide at position 637 that defined by the nucleic acid sequence shown in FIG. 1b, extending from the end constituted by the nucleotide at position 638 to that constituted by the nucleotide at position 745, that defined by the nucleic acid sequence shown in FIG. 1b, extending from the end constituted by the nucleotide at position 1313 to that constituted by the nucleotide at position 1513, that defined by the nucleic acid sequence shown in FIG. 1b, extending from the end constituted by the nucleotide at position 1679 to that constituted by the nucleotide at position 1843, that defined by the nucleic acid sequence shown in FIG. 1b, extending from the end constituted by the nucleotide at position 1844 to that constituted by the nucleotide at position 2022, that defined by the nucleic acid sequence shown in FIG. 1b, extending from the end constituted by the nucleotide at position 638 to that constituted by the nucleotide at position 1843. or their complementary nucleotide sequence;

these are sequences which have been derived from those of FIG. 1b and they may be used under the hybridization conditions described by Maniatis et al. in "Molecular cloning", Cold Spring Harbor Laboratory, 1982.

The synthesis of the cDNA strand and its subsequent in vitro amplification may also be carried out by using the PCR (Polymerase Chain Reaction) method, as described for example by Goblet et al. in *Nucleic Acid Research*, 17, 2144, 1989 "One step amplification of transcripts in total RNA using Polymerase Chain Reaction", by using two chemically synthesized amplimers defined from the sequence of FIG. 1b. Suitable amplimers are for example: that defined in FIG. 1b from nucleotide 638 to nucleotide 667 and that defined in FIG. 1b from nucleotide 1815 to nucleotide 1843.

The amplified fragment of nucleic acids may then be cloned according to the procedures described in Ausubel F. M., Brent R., Kingston R. E., Moore D. D., Smith J. A., Seidman J. G. and Struhl K. (1989) *Current Protocols in Molecular Biology*, chapter 3, Greene Publishing Associates and Wiley-Interscience, New York.

The invention also relates to recombinant vectors in particular for cloning and/or expression, in particular of the plasmid, cosmid or phage type, containing a nucleic acid of the invention at one of its sites not essential for its replication.

The invention also relates to the vector M13mp18-Huβ3, (No. 1085), constituted by a bacteriophage deposited under the No. I-833 on Jan. 20, 1989 with the CNCM, 25 rue du Docteur Roux, Paris.

A suitable vector of the invention contains at one of its sites not essential for its replication elements necessary to promote the expression of a polypeptide according to the invention in a cell host and possibly a promoter recognized by the polymerases of the cell host, in particular an inducible promoter and possibly a signal sequence and an anchoring sequence.

The invention also relates to a cell host transformed by a recombinant vector previously defined comprising the elements of regulation making possible the expression of the nucleotide sequence coding for one of the polypeptides according to the invention in this host.

By cell host is meant any organism capable of being maintained in culture.

One of the microorganisms used may be constituted by a bacterium, in particular *Eschericia coli.*

An organism of choice is constituted by an eucaryotic organism such as CHO (Chinese Hamster Ovary) cells.

However, other organisms may be used just as readily, naturally provided that there are available for each of them vectors, in particular plasmid vectors, capable of replicating in them and nucleotide sequences which can be inserted into these vectors and which are capable, when they are followed in these vectors by an insert coding for a polypeptide of the invention, of ensuring the expression of this insert in the selected organisms and their transport into the membrane of the cell hosts.

The invention also relates to the antibodies directed specifically against one of the polypeptides of the invention, these antibodies being such that they recognize neither the β1 adrenergic receptor nor the β2 adrenergic receptor. In particular, these antibodies recognize the following amino acid sequences:

| | |
|---|---|
| 1 to 36 | 178 to 201 |
| 64 to 74 | 223 to 291 |
| 101 to 108 | 314 to 325 |
| 133 to 135 | 345 to 402 |

In order to produce the antibodies, one of the above-mentioned polypeptides may be injected into an animal.

Monoclonal antibodies are prepared by cell fusion between myeloma cells and spleen cells of immunized mice according to standard procedures.

The invention also relates to the synthetic or non-synthetic nucleotide probes which hybridize with one of the nucleic acids defined above or with their complementary sequences or their corresponding RNA, these probes being such that they hybridize neither with the gene nor the messenger RNA of the β1 and β2 adrenergic receptors.

The probes of the invention contain a minimum of 10 and advantageously 15 nucleotides and may contain maximally the entire nucleotide sequence shown in FIG. 1b.

In the case of the shortest probes, i.e. those of about 10 to about 100 nucleotides, suitable hybridization conditions are the following: 750 mM of NaCl, 75 mM of tri-sodium citrate, 50 μg/ml of salmon sperm DNA, 50 mM of sodium phosphate, 1 mM of sodium pyrophosphate, 100 μM of ATP, 10 to 25% of formamide, 1% Ficoll (Pharmacia, mean molecular weight of 400,000), 1% polyvinylpyrrolidone, 1% bovine serum albumin—for 14 to 16 h at 42° C.

In the case of the longest probes, i.e. possessing more than about 100 nucleotides, suitable hybridization conditions are those previously indicated for the shortest probes but in which the medium defined above contains 40% of formamide instead of 10 to 25% of formamide and contains, in addition, 10% of dextran sulfate.

The invention relates in particular to the following nucleotide probes:

that defined by the nucleic acid sequence shown in FIG. 1b, extending from the end constituted by the nucleotide at position 1 to that constituted by the nucleotide at position 637 that defined by the nucleic acid sequence shown in FIG. 1b, extending from the end constituted by the nucleotide at position 638 to that constituted by the nucleotide at position 745 that defined by the nucleic acid sequence shown in FIG. 1b, extending from the end constituted by the nucleotide at position 1313 to that constituted by the nucleotide at position 1513, that defined by the nucleic acid sequence shown in FIG. 1b, extending from the end constituted by the nucleotide at position 1679 to that constituted by the nucleotide at position 1843, that defined by the nucleic acid sequence shown in FIG. 1b, extending from the end constituted by the nucleotide at position 1844 to that constituted by the nucleotide at position 2022, that defined by the nucleic acid sequence shown in FIG. 1b, extending from the end constituted by the nucleotide at position 638 to that constituted by the nucleotide at position 1843.

The polypeptides of the invention may be prepared by culture in a suitable medium of a cell host previously transformed by a recombinant vector containing one of the nucleic acids previously defined and by recovery from the above-mentioned culture of the polypeptide produced by the said transformed cell host.

Another process for the preparation of the polypeptides of the invention is characterized in that, starting preferably from the C-terminal amino acid, successive amino acids are condensed stepwise in the required order or amino acids are condensed with previously formed fragments which already contain several amino acid residues in the required order or also several fragments previously so prepared are condensed, it being understood that it will be necessary to protect beforehand all of the reactive functions borne by these amino acids or peptide fragments with the exception of the amine function of the one and the carboxyl function of the other, or vice versa, which are normally required to participate in the formation of the peptide bonds, in particular after activation of the carboxyl function, according to the known methods in peptide synthesis and so on stepwise until the N-terminal amino acid is reached.

When the expression of the β3 adrenergic receptors is to be produced in a bacterium, such as E. coli or in a eucaryotic cell such as a CHO cell, the following steps are performed:

the transformation of a competent cell host with a vector, in particular a plasmid or a phage, in which a sequence of nucleotides coding for the β3 receptor (insert) has previously been inserted under the control of regulatory elements, in particular a promoter recognized by the polymerases of the cell host and making possible the expression in the cell host used of the said sequence of nucleotides, the culture of the transformed cell host under conditions allowing the expression of the said insert, and the transport of the β3 receptor expressed toward the membrane such that the transmembrane sequences of the β3 receptor are exposed at the surface of the transformed cell host.

When expression is to be obtained in eucaryotic cells, the regulatory elements may include the endogenous promoter for the adrenergic receptors or viral promoters such as those of SV40 virus or the Rous sarcoma virus (RSV).

When expression is to be obtained in E. coli, the regulatory elements may include the promoter of the lactose operon or the tryptophan operon.

The invention also relates to a process for the detection of the capacity of a molecule to behave as a ligand towards a peptide of the invention, such a procedure comprises:

the placing in contact of the molecule with a cell host previously transformed by a vector, itself modified by an insert coding for the above-mentioned polypeptide, this host bearing at its surface one or more specific sites for this polypeptide, where appropriate, after induction of the expression of this insert, this placing in contact being performed under conditions allowing the formation of a bond between at least one of these specific sites and the said molecule once it has been proved effectively to possess an affinity for this polypeptide, the detection of the possible formation of a complex of the ligand-polypeptide type.

The invention also relates to a process for the study of the affinity of a polypeptide of the invention for one or more specific ligands, with this process comprising:

the transformation of a competent cell host with a vector, in particular a plasmid or a phage, in which a nucleotide sequence coding for the β3 receptor (insert) has previously been inserted, under the control of regulatory elements, in particular a promoter recognized by the polymerases of the cell host and which allow the expression in the cell host used of the said sequence of nucleotides, the culture of the transformed cell host under conditions allowing the expression of the said insert, and the transport of the β3 receptor expressed towards the membrane such that the transmembrane sequences of the β3 receptor are exposed at the surface of the transformed cell host, the placing in contact of this cell host with specific ligands, the detection of an affinity reaction between the said transformed cell host and the said specific ligands.

The procedure described above also makes possible the identification of the "fragments containing the sites" referred to previously and which contain only a part of the sequence of 402 amino acids of FIG. 12.

This identification consists of using inserts shorter than the nucleic acid coding for the above-mentioned sequence, of implementing the steps relating to the expression, the transport of the expression product and the exposure referred to above. When the expression, the transport of the expression product and its exposure on the membrane are obtained, as well as the reaction with the ligands as previously defined, it is then possible to determine the fragments containing the essential sites. Consequently, the absence of reaction with the ligands, as previously defined, by using fragments shorter than the complete sequence, would tend to show that some essential sites have been eliminated.

The invention also relates to a kit for the detection of the possibly affinity of a ligand for a polypeptide of the invention, with said kit comprising:

a culture of cell hosts transformed by a modified vector such as previously defined or a culture of cell hosts previously defined, physical or chemical agents to induce the expression of the nucleotide sequence contained in the modified vector when the promoter placed upstream from this sequence is a promoter inducible by the said chemical or physical agents, and to produce a protein, one or more control ligands having specific affinities for the above-mentioned polypeptide, physical or chemical agents for the characterization of the biological activity of the protein expressed.

The invention also relates to a screening process for medicines intended for the treatment of obesity, fatty diabetes, as well as hyperlipidemias.

BRIEF DESCRIPTION OF THE FIGURES

FIGS. 1A and 1B represent the protein and DNA sequences of a novel β-adrenergic receptor, in which FIG. 1A is a comparison of β1, β2 and β3-adrenergic receptor protein sequences and FIGS. 1B-1, 1B-2 and 1B-3 show the DNA sequences of a novel β-adrenergic receptor.

DETAILED DESCRIPTION OF THE PREFERRED EMBODIMENTS

Other characteristics and advantages of the invention will become apparent in the remainder of the description and the examples, in particular in relation to the drawings and figures in which:

FIG. 12 represents the amino acid sequences of the human β1 adrenergic receptor (second line), the human β2 adrenergic receptor (third line), aligned with those of the human β3 adrenergic receptor (first line). In the sequences of the β1 and β2 adrenergic receptors the positions bearing amino acid residues identical with those of the β3 adrenergic receptor are indicated by dashes.

In order to demonstrate the homologies, deletions have been made in the three sequences and these deletions are represented by the spaces between square brackets.

The seven hydrophobic regions of 21 to 27 residues which are considered to form the Δ-helical transmembrane domains are indicated by thick lines and delimit extra-cellular and intra-cellular loops, the extra-cellular loops being represented by 01–04 in the Figure and the intra-cellular loops by i1 to i4.

In the N-terminal extra-cellular regions of the three receptors, the consensus sequences for the glycosylation sites linked to asparagine (NXS/T) are underlined, it being recalled that in the representation of the amino acids according to DAYHOFF, N represents asparagine, S represents serine, T represents threonine, X represents any amino acid.

In the third intra-cellular loop and in the C-terminal region, triangles show the Ser and Thr residues which are probably implicated in the desensitization of the receptor.

FIGS. 2A and 2B represents the accumulation of cyclic AMP in CHO-β3 cells cells after exposure to (FIG. 2A), (1)-isoproterenol (▲), (1)-noradrenalin (○), (1)-adrenalin (●) or (d)-isoproterenol (▽) and (FIG. 2B); BRL 37344 (■), oxprenolol (□), pindolol (○) or salbutamol (●). The $K_{act}$(nM) values are: 3.86±0.43 for (1)-isoproterenol, 5.65±1.32 for BRL 37344, 6.28±0.80 for noradrenalin, 47.4±6.9 for adrenalin, 76.3±1.57 for oxprenolol, 108±3 for (d)-isoproterenol, 167±10 for pindolol and 273±25 for salbutamol.

In these experiments, the accumulation of cyclic AMP varies from 300% to 400% compared with base levels and the results are expressed as % of the maximal response (mean±standard deviation /n=4 to n=6/) induced by each of the ligands. In the CHO cells, neither noradrenalin, nor adrenalin, nor isoproterenol activates the adenylate cyclase.

The agonist procaterol, specific for β2, stimulates the adnylate cyclase at concentrations higher than $10^{-5}$M (not shown).

Figure 2D:
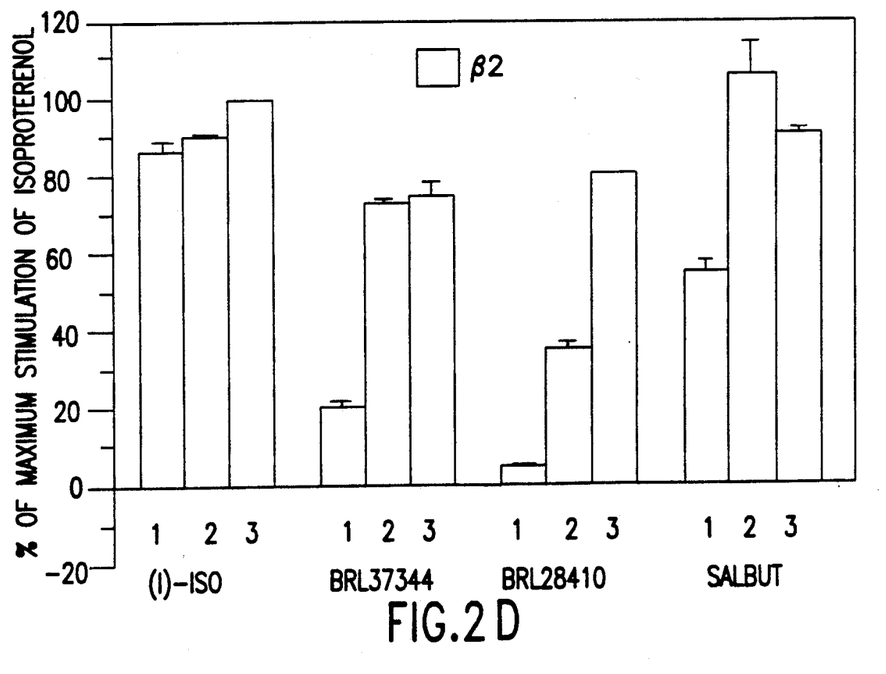
Figure 2E:
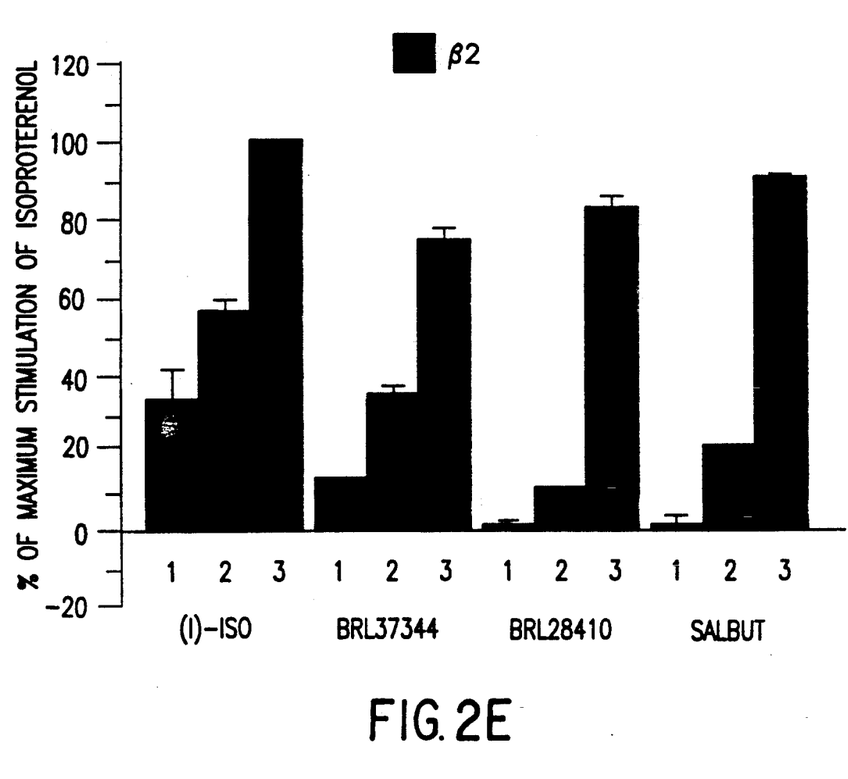

FIGS. 2C, 2D, and 2E shown stimulation of cyclase by isoproterenol, BRL 37344, BRL 28140 and salbutamol in CHO cells expressing β1, β2 or β3 genes. For each of the panels, the results are the means of two or three experiments done twice. Half of the standard deviation is shown for each by vertical bars. Three concentrations of ligands were used: $5 \times^{-9}$ (1), $5 \times 10^{-7}$ (2) and $10^{-4}$ (3).

The results represent the % mean ± standard deviation (n=4 to 6)/ of the response induced by $10^{-4}$ M isoproterenol.

Figure 4:
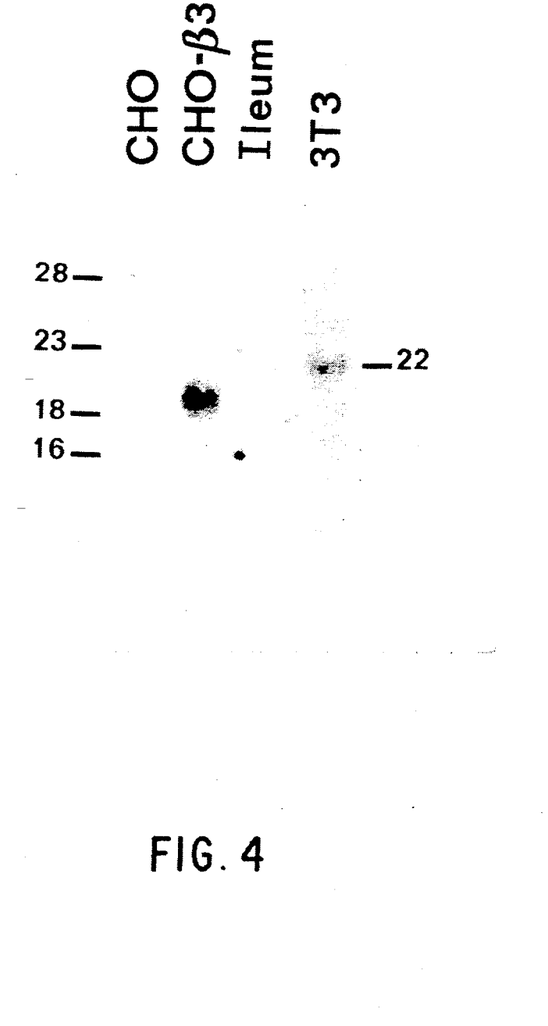
FIG. 4 is schematic expression of the β3-adrenergic receptor gene demonstrated by hybridization of the RNA with a specific probe for the β3-adrenergic receptor.

The method used is the following: the coding region of the gene for the β3 adrenergic receptor was inserted under the control of a SV40 promoter in an expression vector (20) which also contains the gene for murine dihydrofolate reductase (DHFR) used for the selection of the transfected cells. This construction was introduced into CHO cells (21) deficient in DHFR, giving rise to resistant colonies on selective media from which stable sub-clones are obtained. The expression of the β3 adrenergic receptor gene is demonstrated by hybridization of the RNA with a specific probe for the β3 adrenergic receptor (FIG. 4). For the cyclic AMP assay, cells are cultivated and harvested after treatment with ethylenediamme tetracatic acid (Eurobio, Paris), washed and resuspended in a Hank medium containing 20 mM of Hepes buffered at pH 7.4, 1 mM ascorbic acid and 0.1 mM isobutyl-methyl-xanthine. Aliquots of $10^6$ cells are incubated for 30 min. in a total volume of 1 ml with the indicated concentrations of agonists and the cAMP levels are measured according to the specifications of the Amersham assay kit.

Figure 3:
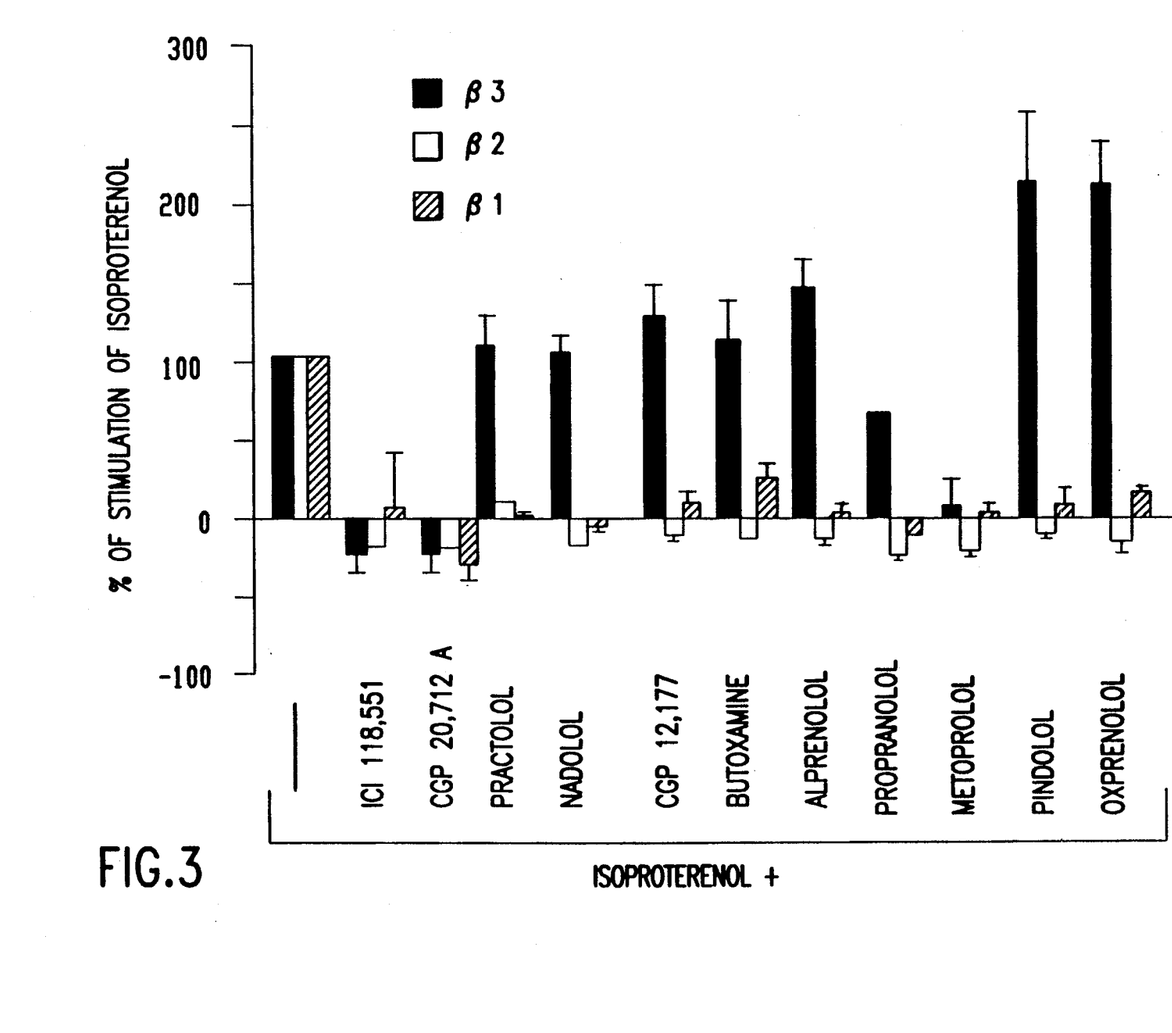
FIG. 3 represents, graphically, the inhibition by the β-adrenergic antagonists of the accumulation of cyclic AMP induced by isoproterenol in β1-CHO, β2-CHO and β3-CHO cells.

FIG. 3 represents the inhibition by the β-adrenergic antagonists of the accumulation of cyclic AMP induced by isoproterenol in β1-CHO, β2-CHO and β3-CHO cells. The results are expressed in %/mean±SD (n=4 to 6) of the accumulation of cyclic AMP induced by isoproterenol alone. The compounds ICI, 118551 (manufactured by the IMPERIAL CHEMICAL INDUSTRY company) and CGP 20712A (manufactured by the CIBA-GEIGY company) block the accumulation of cyclic AMP with calculated Ki of 0.77±0.08 μM and 6.70±0.87 μM, respectively. Metropol has no effect at concentrations lower than $10^{-5}$M.

The method used is the following: the cells, as in FIG. 2, are incubated for 30 min. with the inhibitors at $10^{-4}$M before the addition of $5.10^{-9}$M of isoproterenol. The incubation is continued for a further 30 min. and the levels of cyclic AMP are measured.

FIG. 4 represents the Northern Blot analyses of RNA from tissues and line cells. The RNA to be analysed is obtained from rat tissues (2 μg of RNA polyA+ from: total brain, cortex, hippocampus, hypothalamus, hypophysis, olfactory bulb, striatum, cerebellum, ileum, liver, heart, lung, kidney, skin and muscle) and human cell lines (5 μg of RNA polyA+ of: neuroblastomas, lung and fibroblasts of lung and epidermis, B and T lymphocytes, erythroblasts and myeloblasts). None of these RNAs give any detectable signal (the results are shown for the ileum). A specific messenger is detected in the RNA (15 μg of total RNA) from adipose cell lines 3T3-F442A or from transfected β3-CHO cells. The S values for the molecular weight markers of RNA are shown in the lefthand margin.

The method used is the following: the RNA is subjected to electrophoresis on a 0.7% agarose gel, transferred to nylon membranes and hybridized with probes specific for the β3 adrenergic receptors radioactively labelled by the random initiation method. This probe is derived from the third intracytoplasmic loop of the β3 adrenergic receptor, the sequence of which is weakly conserved between the three receptors (positions 1313 to 1513 of FIG. 1b). Following hybridization, the filters are washed in 0.1×SSC (i.e. 0.015M NaCl and 0.0015M sodium citrate, pH 7.0)+0.05% SDS at 55° C. Under these conditions, no signal is obtained with the RNA prepared from CHO cells expressing the β1 or β2 adrenergic receptor.

EXAMPLE

Determination and expression of the human β3 adrenergic receptor in CHO cells A human genomic library was investigated with the entire coding regions of the gene for the β1 adrenergic receptor of the turkey (14) and of the human gene for the β2 adrenergic receptor (8). The genes coding respectively for the human β1 and β2 adrenergic receptors were identified among the positive clones. The homology between their coding regions is 48.9%. Other clones were obtained containing a gene without an intron, the coding region of which shows 50.7% and 45.5% of homology with the coding regions of β1 and β2, respectively (FIG. 1a). This gene was designated as the gene for the β3 adrenergic receptor. More precisely, in FIG. 1a, each group of three lines corresponds to β3 in the case of the first line, to β1 in the case of the second line and to β2 in the case of the third line.

The gene for the β3 adrenergic receptor codes for a polypeptide of 402 amino acid residues (molecular weight 42881D) which possesses the main characteristics common to the other membrane receptors of the $R_7G$ family (FIG. 1a). It possesses seven groups of 21 to 27 essentially hydrophobic amino acids, likely to constitute α-helical transmembrane domains. These transmembrane domains play an important role in the formation of the recognition sites of the catecholamines by the β-adrenergic receptors (15-18) and are certainly the most homologous regions between the three proteins β1, β2 and β3 (FIG. 1a). In particular, the Asp residues at positions 79 and 113 of the β2 adrenergic receptor, which may act as counter-ions to the positively charged amine of the adrenergic ligands (18), are conserved at similar positions of the β3 adrenergic receptor. Other functionally important residues such as the Cys residues at positions 106 and 184, Asn at position 318 and Pro at position 323 of the sequence of the β2 adrenergic receptor are present at the corresponding positions in the β3 adrenergic receptor.

Like the other $R_7G$ proteins, the β3 adrenergic receptor contains in its amino terminal region consensus sequences for the glycosylation sites associated with Asn. In its third intra-cytoplasmic loop and in its C-terminal region, the β3 adrenergic receptor possesses several Ser and Thr residues surrounded by basic residues (Arg and Lys) and residues which break up the α-helical structure (Pro and Gly), which may serve as substrates for the kinases possibly involved in the desensitization of the receptor (19).

In order to better characterize the β3 adrenergic receptor, its gene was transfected into CHO cells and several clones producing the corresponding RNA were stabilized. These cells are designated as "β3-CHO" cells. CHO cells expressing either the gene for the β1 adrenergic receptor or the gene for the β2 adrenergic receptor were also prepared in order to compare the pharmacological properties of the three receptors in an identical environment. These cells are designated as β1-CHO and β2-CHO cells. The β3-CHO cells synthesize a protein of an apparent molecular weight of about 65000D, which may be visualized by affinity labelling with $^{125}$I-iodocyanopindololdiazirine. The post-transcriptional addition of sugar residues to one or two glycosylation sites at the amino-terminus of the β3 adrenergic receptor is certainly responsible for this molecular weight being higher than that deduced from the amino acid sequence.

The exposure of the β3-CHO cells to β-adrenergic agonists (FIG. 2) such as adrenalin, noradrenalin, isoproterenol, salbutamol, BRL 28410 or BRL 37344 increases the intracellular concentration of cyclic AMP between 300% and 400% compared with basal levels, whereas there is no effect on non-transfected CHO cells. This affect is stereospecific, in view of the fact that (1)-isoproterenol is almost 30 times more potent than (d) isoproterenol in the activation of the cyclase. Other β-agonists such as procaterol and CGP 361A lead to a stimulation of the cyclase only when they are used at concentrations higher than $10^{-5}$M.

The order in which the following compounds: (1)-isoproterenol, BRL 37344, BRL 28410 and salbutamol activate the adenylate cyclase in the β3-CHO cells is clearly different from that obtained for the responses mediated by the β1 or β2 adrenergic receptors (FIG. 2C). In the case of the β3-CHO cells, this order is similar to that determined for the stimulation of lipolysis in rat adipose cells. The only difference is the relative order of isoproterenol compared with BRL 37344. However, in the reference cited, it was racemic (dl)-isoproterenol which was used whereas in the invention, the levo-rotatory (1)-isoproterenol was used.

The analysis of the capacity of several classical β-antagonists to block the activation of the adenylate cylase stimulated by isoproterenol was carried out in β3-CHO cells (FIG. 3). Apart from ICI 118,551, CGP 20,712A and metoprolol, none of these compounds used at $10^{-4}$M is capable of inhibiting this effect. At concentrations lower than $10^{-5}$M, metoprolol no longer has an effect and ICI 118,551 and CGP 20,712A block the accumulation of cyclic AMP with Ki of $0.77\pm0.08$ μM and $6.70\pm0.87$ μM, respectively. In agreement with these results, neither the intact β3-CHO cells nor their membrane fractions display specific and saturable binding of alprenolol or CGP 12,177 labelled with $^3$H. Furthermore, the $K_D$ of $^{125}$I-iodocyanopindolol for the β3-adrenergic receptor ($488\pm90$ pM) is about 10 times higher than that for the β1 or β2 adrenergic receptors.

According to in vitro studies, pindolol and oxprenolol are considered to be β-adrenergic antagonists. However, they are also considered to be partial agonists because in vivo they may exhibit a slight sympathomimetic activity (22). In the CHO cells transfected with a single type of receptor, these compounds are complete agonists towards the β3-adrenergic receptor (FIG. 2), whereas they totally block the accumulation of cyclic AMP mediated by the β1 and β2 adrenergic receptors (FIG. 3).

This new subtype of β-adrenergic receptor might be able to modulate various functions such as lipolysis, the secretion of insulin or intestinal relaxation. The contractions of the guinea pig ileum induced by the cholinergic pathway are modulated by adrenergic agonists. However, in spite of the total blockage of the α and β-adrenergic receptors with phentolamine and propanolol, isoproterenol can always inhibit the occurrence of contractions. The β3 receptor exhibits a low affinity for propanolol and other classic β blockers, but shows a marked response toward the agonist BRL 37344, which is a powerful stimulant of lipolysis in adipose tissue (1).

The hypothesis, according to which the β3 receptor is present in adipose tissues was confirmed by the analysis of the capacity of the RNA derived from tissues of various origins to hybridize with probes specific for the β3-adrenergic receptor (FIG. 4): a hybridization signal with the probes used was observed only with the RNA of the adipocyte line 3T3-F442A (23),

This β3-adrenergic receptor might also be implicated in the regulation by the catecholamines of the action of insulin on the metabolism of glucose and fatty acids.

REFERENCES

1. Arch, J. R. S., Ainsworth, A. T., Cawthorne, M. A., Piercy, V., Sennitt, M. V., Thody, V. E., Wilson, C. and Wilson, S. (1984), Nature 309, 163–165.
2. Jacobson, B., Vauquelin, G., Wesslau, C., Smith, U. and Strosberg, A. D. (1981), Eur. J. Biochem. 114, 349–354.
3. Bond, R. A. and Clarke, D. E. (1987), Br. J. Pharmac. 91, 683–686.
5. Cotecchia, S., Schwinn, D. A., Randall, R. R., Lefkowitz, R. J., Caron, M. G. and Kobilka, B. K. (1988), Proc. Natl. Acad. Sci. USA 85, 7159–7163
6. Kobika, B. K., Matsui, H., Kobika, T. L., Yang-Feng, T. L., Francke, U., Caron, M. G., Lefkowitz, R. J. and Regan, J. W. (1987), Science 238, 650–656.
7. Frielle, T., Collins, S., Daniel, K. W., Caron, M. G., Lefkowitz, R. J. and Kobilka, B. K. (1987), Proc. Natl. Acad. Sci. USA 84, 7920–7924.
8. Emorine, L. J., Marullo, S., Delavier-Klutchko, C., Kaveri, S. V., Durieu-Trautman, O. and Strosberg, A. D. (1987), Proc. Natl. Acad. Sci. USA 84, 6995–6999.
9. Dixon, R. A. F., Strader, C. D. and Sigal, I. S. (1988), Annual Reports in Medicinal chemistry, 221–233. Ed. Seamon, K. B., Food and Drug Administration, Bethesda, Md 20892.
10. Emorine, L. J., Marullo, S., Sutren, M., Delavier, C., Eshdat, Y., Raposo, G. and Strosberg, A. D. (1988), Proc. NATO Adv. Res. Workshop: "Molecular biology of neuroreceptors and ion channels", Santorini, Ed. by A. Maelicke (in the press).
11. Bonner, T. I., Young, A. C., Brann, M. R. and Buckley, N. J. (1988), Neuron 1, 403–410.
12. Regan, J. W., Kobilka, T. S., Yang-Feng, T. L., Caron, M. G., Lefkowitz, R. J. and Kobilka, B. K. (1988), Proc. Natl. Acad. Sci. USA 85, 6301–6305.
13. Bahouth, S. W. and Malbon, C. C. (1988), Molec. Pharmacol. 34, 318–328.
14. Yarden, Y., Rodriguez, H., Wong, S. K. F., Brandt, D. R., May, D. C., Burnier, J., Harkins, R. N., Chen, E. Y., Ramachandran, J., Ullrich, A. and Ross, E. M. (1986), Proc. Natl. Acad. Sci. USA 83, 6795–6799.
15. Dixon, R. A. F., Sigal, I., Candelore, M. R., Register, R. B., Scattergood, W., Rands, E. and Strader, C. D. (1987), EMBO J. 6, 3269–3275.
16. Dohlman, H. G., Caron, M. G., Strader, C. D., Amlaiky, N. and Lefkowitz, R. J. (1988), Biochem. 27, 1813–1817.
17. Kobilka, B. K., Kobilka, T. S., Daniel, K., Regan, J. W., Caron, M. G. and Lefkowitz, R. J. (1988), Science 240, 1310–1316.
18. Strader, C. D., Sigal, I. S., Candelore, M. R., Rands, E., Hill, W. S. and Dixon, R. A. F. (1988), J. Biol. Chem. 263 10267–10271.
19. Bouvier, M., Hausdorff, P., De Blasi, A., O'-Dowd, B. F., Kobilka, B. K., Caron, M. G. and Lefkowitz, R. J. (1988), Nature 333, 370–373.
20. Larsky, L. A., Dowbenko, D., Simonsen, C. C. and Berman, P. W. (1984), Biotechnology 2, 527–532.
21. Uriaub, G. and Chasin, L. A. (1980), Proc. Natl. Sci. U.S.A. 77, 4216–4220.
22. Goodman and Gilman's (1980), The pharmacological basis of therapeutics 6th ed., Macmillan Publishing Co., Inc.
23. Green, H. and Kehinde, O. (1976), Cell 7, 105–113.

What is claimed is:

1. A substantially pure polypeptide having a β-adrenergic receptor activity comprising: the sequence of 402 amino acids of FIG. 12, or a fragment of said sequence, wherein said fragment contains sites in this sequence such that when this fragment is exposed at the surface of a cell, it is capable of participating in the activation of adenylate cyclase in the presence of an agonist, this activation increasing in the order of the agonists as follows: salbutamol, (1)-isoproterenol or said fragment is capable of being recognized by antibodies which also recognize the above-mentioned sequence of 402 amino acids, but which do not recognize the β1-adrenergic receptor or the β2-adrenergic receptor, or said fragment is capable of generating antibodies which recognize the above-mentioned sequence of 402 amino acids but do not recognize either the β1-adrenergic receptor or the β2-adrenergic receptor.

2. The polypeptide according to claim 1, wherein said polypeptide has the capacity to stimulate adenylate cyclase and/or accumulate cAMP induced by isoproterenol and is not inhibited by practolol, nadolol, butoxamine, alprenolol, propanolol, pindolol, oxprenolol, at concentrations lower than or equal to $10^{-4}$M under conditions wherein: cells are cultivated and harvested after treatment with ethylenediamine tetraacetic acid, washed and resuspended in a Hank medium containing 20 mM of Hepes buffered at pH 7.4, 1 mM ascorbic acid and a1 mM isobutyl-methyl-xanthine; aliquots of $10^6$ cells are incubated for 30 minutes with the inhibitors at $10^{-4}$M before the addition of $5.10^{-9}$M of isoproterenol; the incubation is continued for a further 30 minutes and the cyclic AMP levels are measured to test for the accumulation of cyclic AMP.

3. The polypeptide according to claim 2, wherein pindolol and oxprenolol stimulate adenylate cyclase and/or the accumulation of cyclic AMP in CHO cells transfected with said polypeptide under conditions wherein cells are cultivated and harvested after treatment with ethylenediamine tetraacetic acid (Eurobio, Paris), washed and resuspended in a Hank medium containing 20 mM of Hepes buffered at pH 7.4, 1 mM of ascorbic acid and 0.1 mM of isobutyl methyl-xanthine; aliquots of $10^6$ cells are incubated for 20 minutes in a total volume of 1 ml with concentrations of pindolol or oxprenolol higher than $10^{-11}$M and the cAMP levels to test for the accumulation of cyclic AMP.

4. A nucleic acid consisting of a chain of nucleotides coding for the polypeptides according to claim 1.

5. A nucleic acid according to claim 4, consisting of the chain of nucleotides shown in FIG. 1a, extending from the end constituted by nucleotide 1 to that constituted by nucleotide 2022.

6. A recombinant vector comprising a nucleic acid according to claim 4 at one of its sites not essential for its replication.

7. The recombinant vector according to claim 6, wherein said vector is M13mp18-Huβ3, (No. 1085) deposited under the No. I-833 on Jan. 20, 1989 at the CNCM, 25 rue du Docteur Roux, Paris.

8. The recombinant vector according to claim 6, wherein said vector comprises at one of its sites not essential for its replication elements necessary to promote the expression of one of the amino acid sequences according to claim 1 in a host cell and a promoter recognized by the polymerases of the host cell.

9. A host cell transformed by a recombinant vector according to claim 6, comprising the elements of regulation allowing the expression of the nucleotide sequence coding for the polypeptide.

10. The transformed host cell according to claim 9, wherein said host cell is *E. coli*.

11. The transformed host cell according to claim 9, wherein said host cell is a CHO cell.

12. An antibody directed specifically against a polypeptide according to claim 1, wherein said antibody does not recognize the β1-adrenergic receptor nor the β2-adrenergic receptor and does recognize the following amino acid sequence:

| | |
|---|---|
| 1 to 36 | 178 to 201 |
| 64 to 74 | 223 to 291 |
| 101 to 108 | 314 to 325 |
| 133 to 135 | 345 to 402 | set forth in FIG. 1b.

13. A nucleotide probe wherein said nucleotide probe hybridizes with one of the nucleic acids according to claim 4 or the complementary sequence under conditions of hybridization such that it does not hybridize with the genes or messenger RNA of the β1 or β2 adrenergic receptors, and said probes are selected from the group of nucleotide probes consisting of the nucleic acid sequence shown in FIG. 1b, extending from the end nucleotide at position 1 to the nucleotide at position 637, the nucleic acid sequence shown in FIG. 1b, extending from the end nucleotide at position 638 to the nucleotide at position 745, the nucleic acid sequence shown in FIG. 1b, extending from the end nucleotide at position 1313 to the nucleotide at position 1513, the nucleic acid sequence shown in FIG. 1b, extending from the end nucleotide at position 1679 to the nucleotide at position 1843, the nucleic acid sequence shown in FIG. 1, extending from the end nucleotide at position 1844 to the nucleotide at position 2022, the nucleic acid sequence shown in FIG. 5, extending from the end nucleotide at position 638 to the nucleotide at position 1843, their complementary nucleotide sequence and mixture thereof.

14. Process for the preparation of a polypeptide according to claim 1, characterized in that a host cell previously transformed by a recombinant vector containing a nucleic acid according to the above is cultivated in a suitable medium and the polypeptide produced by the said transformed cell host is recovered from the culture.

15. A process for detecting the binding of an agonist or antagonist to a polypeptide according to claim 1 comprising the steps of:

(a) placing said agonist or antagonist in contact with a host cell previously transformed by a vector modified by an insert coding for said polypeptide wherein said host cell bears at its surface one or more sites specific for said polypeptide under conditions permitting the formation of a bond between at least one of these specific sites and the said agonist or antagonist; and (b) detecting the formation of a complex formed between said antagonist or agonist and said polypeptide.

16. A process to study the affinity of a polypeptide according to claim 1, to one or several ligands comprising the steps of:

(a) transforming a competent host cell with a vector in which a nucleotide sequence coding for the β-3 receptor has been placed beforehand under the control of regulatory elements which allows the expression of the nucleotide sequence in the host cell;

(b) culturing the host cell under conditions allowing the expression of said β-3 receptor and the transport of the β-3 receptor towards the membrane sequences of the β-3 receptor at the surface of said transformed host cell;

(c) contacting the transformed host cell with ligands; and (d) detecting an affinity reaction between said transformed host cell and said ligand.

* * * * *

UNITED STATES PATENT AND TRADEMARK OFFICE
CERTIFICATE OF CORRECTION

PATENT NO. : 5,288,607
DATED : February 22, 1994
INVENTOR(S) : EMORINE et al.

It is certified that error appears in the above-indentified patent and that said Letters Patent is hereby corrected as shown below:

Column 16, line 19, change "FIG. 12" to --FIG. 1a--.

Signed and Sealed this

Third Day of December, 1996

Attest:

BRUCE LEHMAN

Attesting Officer          Commissioner of Patents and Trademarks